US012686655B2

(12) United States Patent
Maduskar et al.

(10) Patent No.: US 12,686,655 B2
(45) Date of Patent: Jul. 21, 2026

(54) METHOD AND SYSTEM FOR LIGHT OLEFIN GENERATION WITH HIGH YIELDS AND SELECTIVITY

(71) Applicant: ExxonMobil Chemical Patents Inc., Baytown, TX (US)

(72) Inventors: Saurabh S. Maduskar, Houston, TX (US); Keith H. Kuechler, Friendswood, TX (US); Xiaoying Bao, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 150 days.

(21) Appl. No.: 18/575,940

(22) PCT Filed: Jul. 5, 2022

(86) PCT No.: PCT/US2022/036093
§ 371 (c)(1),
(2) Date: Jan. 2, 2024

(87) PCT Pub. No.: WO2023/287606
PCT Pub. Date: Jan. 19, 2023

(65) Prior Publication Data
US 2024/0308938 A1 Sep. 19, 2024

Related U.S. Application Data

(60) Provisional application No. 63/329,006, filed on Apr. 8, 2022, provisional application No. 63/222,733, filed on Jul. 16, 2021.

(51) Int. Cl.
*C07C 5/32* (2006.01)
*B01J 8/02* (2006.01)
(Continued)

(52) U.S. Cl.
CPC ............. *C07C 5/325* (2013.01); *B01J 8/0278* (2013.01); *B01J 8/0285* (2013.01); *B01J 23/02* (2013.01);
(Continued)

(58) Field of Classification Search
CPC ....... C07C 7/005; C07C 5/325; C07C 5/3337; C07C 7/00; C07C 11/06; C07C 2523/14;
(Continued)

(56) References Cited

U.S. PATENT DOCUMENTS 6,248,297 B1 6/2001 Stine et al.
10,336,947 B2 * 7/2019 Suriye .................... B01J 29/076
(Continued)

FOREIGN PATENT DOCUMENTS

GB 1107432 A 3/1968
WO 2020/263599 A1 12/2020

*Primary Examiner* — Vishal V Vasisth
(74) *Attorney, Agent, or Firm* — WOMBLE BOND DICKINSON (US) LLP; Kevin Davis

(57) ABSTRACT
A method for forming an olefin, the method including: introducing a hydrocarbon feed stream into a reactor including a dehydrogenation catalyst; reacting the hydrocarbon feed stream with a dehydrogenation catalyst in the reactor to form a high temperature dehydrogenated product, the high temperature dehydrogenated product including at least a portion of the dehydrogenation catalyst; separating at least a portion of the dehydrogenation catalyst from the high temperature dehydrogenated product in a primary separation device and a secondary separation device downstream of and in fluid communication with the primary separation device; following the exit of high temperature dehydrogenation product from the secondary separation device, combining the high temperature dehydrogenation product with a quench stream to cool the high temperature dehydrogenation product and form an intermediate temperature dehydrogenation product, wherein the quench stream includes a hydro-
(Continued)

carbon; and cooling the intermediate temperature dehydrogenation product to form a cooled dehydrogenation product.

18 Claims, 6 Drawing Sheets

(51) Int. Cl.

| | |
|---|---|
| *B01J 23/02* | (2006.01) |
| *B01J 23/62* | (2006.01) |
| *B01J 35/30* | (2024.01) |
| *C07C 7/00* | (2006.01) |

(52) U.S. Cl.
CPC ........... *B01J 23/626* (2013.01); *B01J 35/394* (2024.01); *C07C 7/005* (2013.01); *B01J 2208/00362* (2013.01); *C07C 2521/10* (2013.01); *C07C 2523/62* (2013.01)

(58) Field of Classification Search
CPC ............ C07C 2523/42; C07C 2523/62; C07C 2521/04; C07C 2521/10; C07C 2521/16; B01J 8/0285; B01J 37/0201; B01J 38/12; B01J 37/0045; B01J 23/626; B01J 35/394; B01J 23/96; B01J 8/0278; B01J 23/02; B01J 38/10; B01J 2208/00362
See application file for complete search history.

(56) References Cited

U.S. PATENT DOCUMENTS

| | | | |
|---|---|---|---|
| 11,059,013 B2 | 7/2021 | Pretz | |
| 11,383,225 B2 | 7/2022 | Suriye et al. | |
| 11,987,547 B2 | 5/2024 | Pretz et al. | |
| 2016/0256840 A1 | 9/2016 | Pretz et al. | |
| 2022/0356130 A1* | 11/2022 | Pretz .................... | C07C 5/3337 |

* cited by examiner

METHOD AND SYSTEM FOR LIGHT OLEFIN GENERATION WITH HIGH YIELDS AND SELECTIVITY

CROSS-REFERENCE TO RELATED APPLICATIONS

This application is a 371 of PCT/US2022/036093 filed Jul. 5, 2022. This application claims priority to and the benefit of U.S. Provisional Application No. 63/222,733 having a filing date of Jul. 16, 2021, and U.S. Provisional Application No. 63/329,006 having a filing date of Apr. 8, 2022, the disclosures of which are both incorporated herein by reference in their entireties.

FIELD

Exemplary embodiments of the present technological advancement relate to chemical processing systems, and more specifically to dehydrogenation chemical processing systems.

BACKGROUND

Light olefins may be utilized as base materials to produce many types of goods and materials. For example, ethylene may be utilized to manufacture polyethylene, ethylene chloride, or ethylene oxides. Such products may be utilized in product packaging, construction, textiles, etc. Thus, there is an industry demand for light olefins, such as ethylene, propylene, and butene. Light olefins may be produced by different reaction processes depending on the given chemical feed, which may be a product from a crude oil refining operation or a renewable product from a bio refinery or a natural gas component stream. Many light olefins may be produced through catalytic processes, such as catalytic dehydrogenation, in which the feed stream is contacted with a fluidized catalyst that facilitates conversion of the feed stream into the light olefins. In such systems, reaction selectivity for the light olefins may be important to overall process efficiency.

Patent publication WO 2020/263599, the entirety of which is hereby incorporated by reference, describes a method for forming light olefins that includes introducing a hydrocarbon feed stream into a reactor, reacting the hydrocarbon feed stream with a dehydrogenation catalyst in the reactor to form a high temperature dehydrogenated product, separating at least a portion of the dehydrogenation catalyst from the high temperature dehydrogenated product in a primary separation device, combining the high temperature dehydrogenation product with a quench stream to cool the high temperature dehydrogenation product and form an intermediate temperature dehydrogenation product, and cooling the intermediate temperature dehydrogenation product to form a cooled dehydrogenation product.

Patent publication WO 2018/236630, the entirety of which is hereby incorporated by reference, describes a method for processing a chemical stream that includes contacting a feed stream with a catalyst in an upstream reactor section of a reactor having the upstream reactor section and a downstream reactor section, passing an intermediate product stream to the downstream reactor section, and introducing a riser quench fluid into the downstream reactor section, upstream reactor section, or transition section and into contact with the intermediate product stream and the catalyst to slow or stop the reaction. The method includes separating at least a portion of the catalyst from the product stream, passing the product stream to a product processing section, cooling the product stream, and separating a portion of the riser quench fluid from the product stream. The riser quench fluid separated from the product stream may be recycled back to the downstream reactor section, upstream reactor section, or transition section as the riser quench fluid.

SUMMARY

A method for forming an olefin, the method comprising: introducing a hydrocarbon feed stream into a reactor including a dehydrogenation catalyst; reacting the hydrocarbon feed stream with a dehydrogenation catalyst in the reactor to form a high temperature dehydrogenated product, the high temperature dehydrogenated product including at least a portion of the dehydrogenation catalyst; separating at least a portion of the dehydrogenation catalyst from the high temperature dehydrogenated product in a primary separation device and a secondary separation device downstream of and in fluid communication with the primary separation device; following the exit of high temperature dehydrogenation product from the secondary separation device, combining the high temperature dehydrogenation product with a quench stream, to cool the high temperature dehydrogenation product and form an intermediate temperature dehydrogenation product, wherein the quench stream includes a hydrocarbon; and cooling the intermediate temperature dehydrogenation product to form a cooled dehydrogenation product.

A system for forming an olefin from a hydrocarbon feed stream, the system comprising: a reactor configured to receive the hydrocarbon feed stream under reaction conditions with a dehydrogenation catalyst, wherein the reaction conditions generate a high temperature dehydrogenated product, the high temperature dehydrogenated product including at least a portion of the dehydrogenation catalyst; a plurality of separation devices configured to separate at least a portion of the dehydrogenation catalyst from the high temperature dehydrogenated product, the plurality of separation devices including a primary separation device and a secondary separation device downstream of and in fluid communication with the primary separation device; a quench system configured to combine the high temperature dehydrogenation product with a quench stream to cool the high temperature dehydrogenation product and form an intermediate temperature dehydrogenation product, wherein the quench stream includes a hydrocarbon; and a heat transfer system configured to cool the intermediate temperature dehydrogenation product to form a cooled dehydrogenation product.

DETAILED DESCRIPTION

Definitions

As used herein, and unless otherwise specified, the term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

As used herein, "not formed" means a product formation in the reactor that is not more than 0.1 carbon mole % selectivity (compared to a propane feed) where, (moles of carbon in a product)/(converted moles of carbon in feed) =carbon mole % selectivity of a product. For example, if 2 moles of ethylene is produced when 3 moles of propane is converted, the carbon mole % selectivity of ethylene is 44.4%.

An "olefin," alternatively referred to as "alkene," is a linear, branched, or cyclic compound of carbon and hydrogen having at least one double bond.

Figure 4:
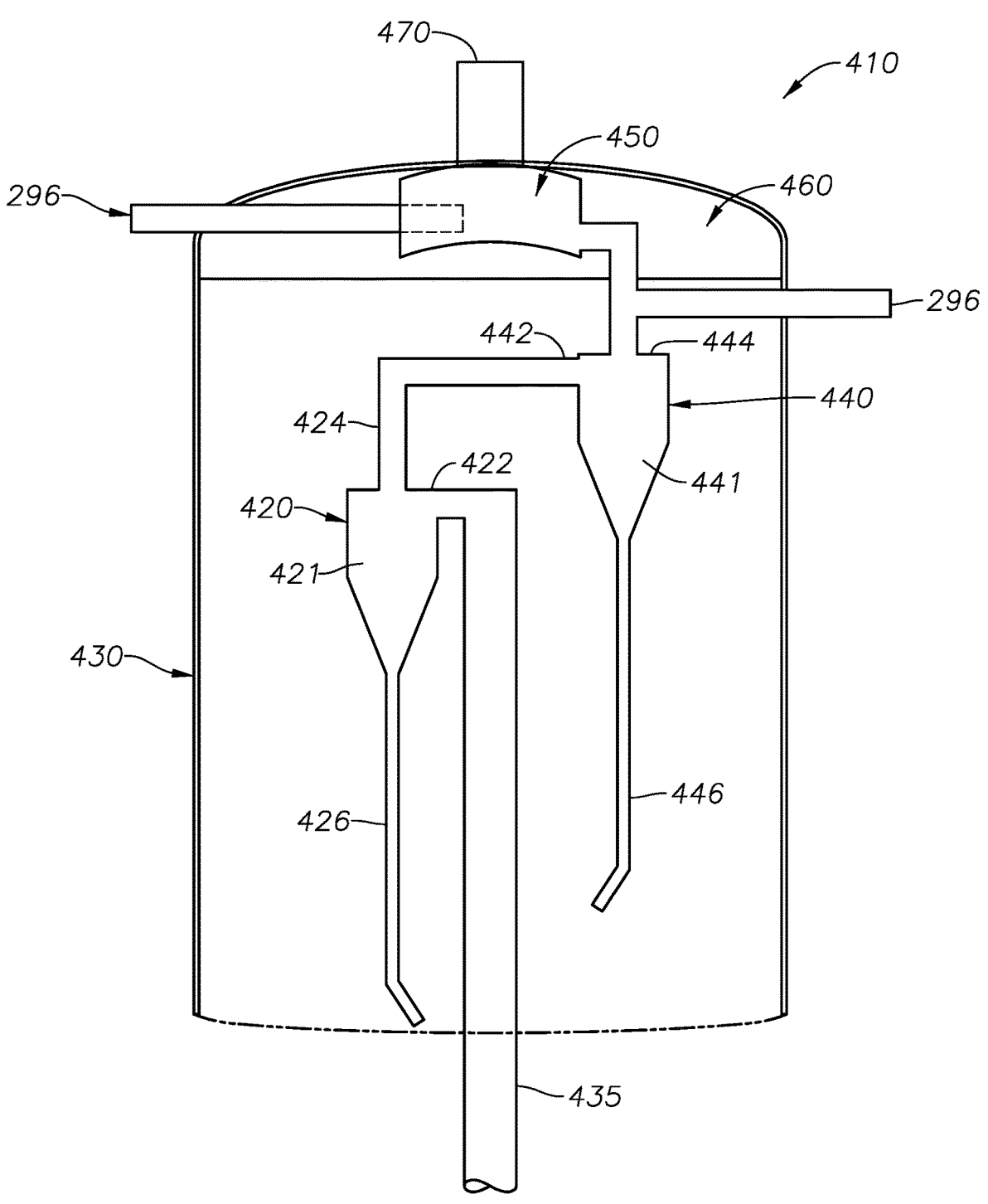
FIG. 4 illustrates a more detailed example of an exemplary reactor embodying the present technological advancement.

"Plenum" means a region of a reactor that facilitates fluid communication between pipes or ducts carrying a hot product stream from reactor to outlet stream. Plenum may also act as a conduit for collecting gases from multiple sets of cyclones before they are exhausted from the reactor. As described below, a reactor can have multiple plenums (first plenum and second plenum as illustrated in FIG. 4, for example), and the term plenum will refer to either of the first or second plenum, unless otherwise noted.

For the purposes of this disclosure, the nomenclature of elements is pursuant to the version of the Periodic Table of Elements (under the new notation) as provided in Hawley's Condensed Chemical Dictionary, 16th Ed., John Wiley & Sons, Inc., (2016), Appendix V. For example, a Group 2 element includes Mg, a Group 8 element includes Fe, a Group 9 element includes Co, a Group 10 element includes Ni, and a Group 13 element includes Al. The term "metalloid", as used herein, refers to the following elements: B, Si, Ge, As, Sb, Te, and At. In this disclosure, when a given element is indicated as present, it can be present in the elemental state or as any chemical compound thereof, unless it is specified otherwise or clearly indicated otherwise by the context.

The term "mixed metal oxide" refers to a composition that includes oxygen atoms and at least two different metal atoms that are mixed on an atomic scale. For example, a "mixed Mg/Al metal oxide" has O, Mg, and Al atoms mixed on an atomic scale and is substantially the same as or identical to a composition obtained by calcining an Mg/Al hydrotalcite that has the general chemical formula $$\left[Mg_{(1-x)}Al_x(OH)_2\right]\left(A_{\frac{x}{n}}^{n-}\right) \cdot mH_2O,$$

where A is a counter anion of a negative charge n, x is in a range of from >0 to <1, and m is ≥0. A material consisting of nm sized MgO particles and nm sized $Al_2O_3$ particles mixed together is not a mixed metal oxide because the Mg and Al atoms are not mixed on an atomic scale but are instead mixed on a nm scale.

The term "selectivity" refers to the production (on a carbon mole basis) of a specified compound in a catalytic reaction. As an example, the phrase "an alkane hydrocarbon conversion reaction has a 100% selectivity for an olefin hydrocarbon" means that 100% of the alkane hydrocarbon (carbon mole basis) that is converted in the reaction is converted to the olefin hydrocarbon. When used in connection with a specified reactant, the term "conversion" means the amount of the reactant consumed in the reaction. For example, when the specified reactant is propane, 100% conversion means 100% of the propane is consumed in the reaction. In another example, when the specified reactant is propane, if one mole of propane convers to one mole of methane and one mole of ethylene, the selectivity to methane is 33.3% and the selectivity to ethylene is 66.7%. Yield (carbon mole basis) is conversion times selectivity.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

While phrases such as hot, high temperature, and intermediate temperature are used herein to describe the reactor and various streams, these terms of degree are used to differentiate streams based on a relative temperature characteristic. Those of ordinary skill in the art will understand that no particular temperature is implied, and that the relative temperature of the streams will be understood in regards to the reactor temperature and heat flow dictated by thermodynamics.

EXEMPLARY EMBODIMENTS

Light olefins (e.g., propylene) can be produced by catalytic process, such as dehydrogenation, in which a feed stream (e.g., propane) is contacted with a fluidized dehydrogenation catalyst at high temperature. The feed stream can be derived from crude oil refinery (e.g. propane). The resultant product mixture can contain a mixture of highly reactive molecules and catalyst particles. Exemplary embodiments of the present technological advancement describe a reactor configuration that can separate catalyst particles from a hot product stream (e.g., about the temperature of the reactor) and subsequently cool the hot product stream using a direct liquid quench to avoid selectivity loss from secondary thermal and catalytic reactions.

Selectivity of light olefins from a dehydrogenation reactor is adversely affected due to secondary reactions. The secondary reactions include continued thermal and catalytic reaction of reactants through side reactions and/or over reaction of products. To avoid this, catalyst particles should be separated from the hot product stream and the resultant hot product stream needs to be cooled to an intermediate temperature sufficiently low to slow or stop the thermal reactions.

Yield and selectivity loss after propylene production by propane dehydrogenation (PDH) reactor can occur due to both thermal and catalytic reactions. These secondary reactions can be minimized by efficient separation of catalyst particles from the high temperature product stream and immediate quench of the high temperature product stream after catalyst separation. A preferred sequence is near-complete catalyst separation with the primary and secondary cyclone separators (i.e., about >98% separation), followed by hydrocarbon quenching. This can be contrasted with a conventional approach of intermediate quenching with partial catalyst separation as described in WO 2020/263599.

A dehydrogenation reactor configured in accordance with the present technological advance can include some or all of the following features: (a) immediate removal of catalyst particles from the product stream after the riser before cooling by using primary and secondary cyclone separators; (b) cooling the high temperature product stream using a direct liquid/gas quench after catalyst separation; (c) use of a quench fluid that is a gas or saturated or subcooled liquid which vaporizes/flashes in fluid contact with the high temperature product stream, which provides efficient contacting for heat transfer; (d) separating the product stream in a downstream separation unit, where at least a portion of the by-product stream from the separator (e.g., benzene) is recycled as a quench fluid; (e) the quench fluid can either be derived from the product stream or it can be an external fluid not formed in the reactor (such as, heavy aromatic solvents) or it can be water; (f) a reaction temperature ranging from 600° C. to 700° C.; (g) the use of a Pt catalyst supported on mixed magnesium aluminum oxide; (h) heat and/or recovery process integration with steam cracker; (i) and fines removal from the product stream after the initial quenching.

Reactor system embodying the present technological advancement can provide some or all of the following advantages: (a) the primary and secondary cyclones can achieve a very high catalyst separation efficiency (>98%) from the high temperature product stream before quench, which minimizes secondary catalytic reactions which can happen even after quench; (b) separated catalyst particles can be circulated to a regenerator at 800° C., wherein higher separation efficiency before quenching avoids sensible heat loss of the catalyst particles; and (c) injecting the quench fluid in the plenum of the reactor reduces reactor design complexity versus the conventional system of WO 2020/263599, in which multiple quench lines would be needed for each separation series.

Figure 1:
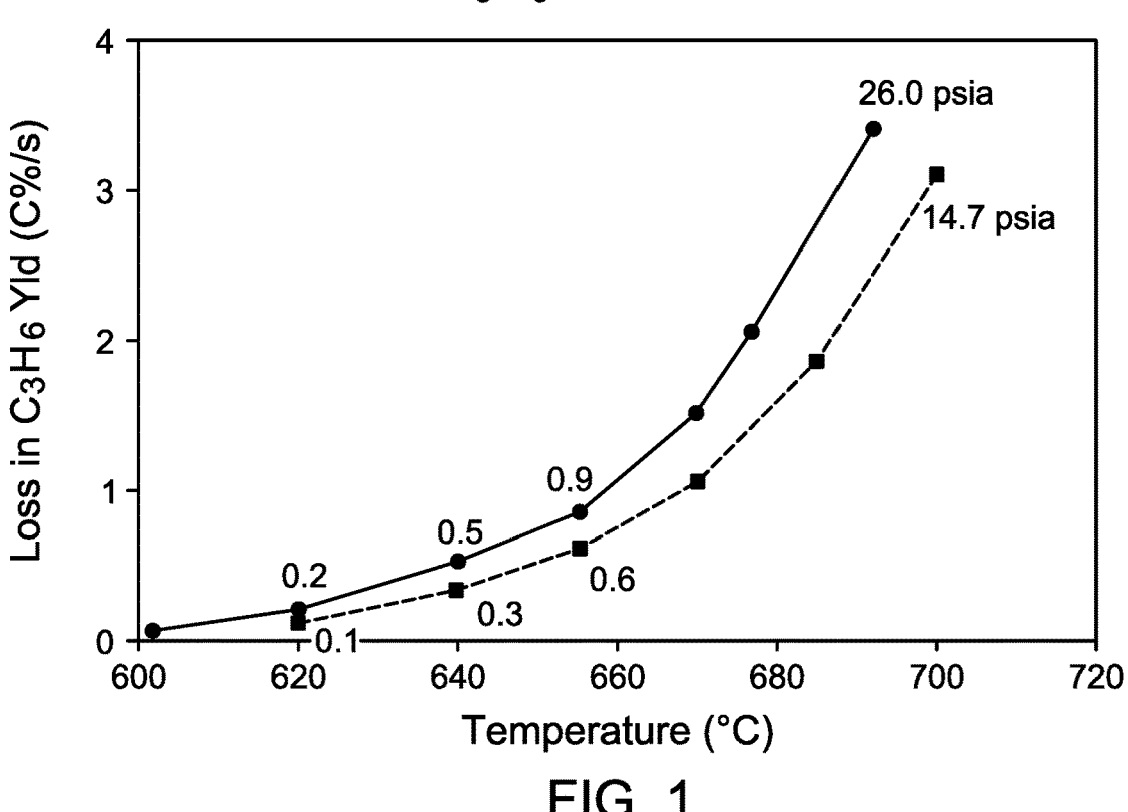
FIG. 1 is a graph illustrating a loss in propylene yield per second due to secondary thermal cracking at different temperatures.
Figure 2:
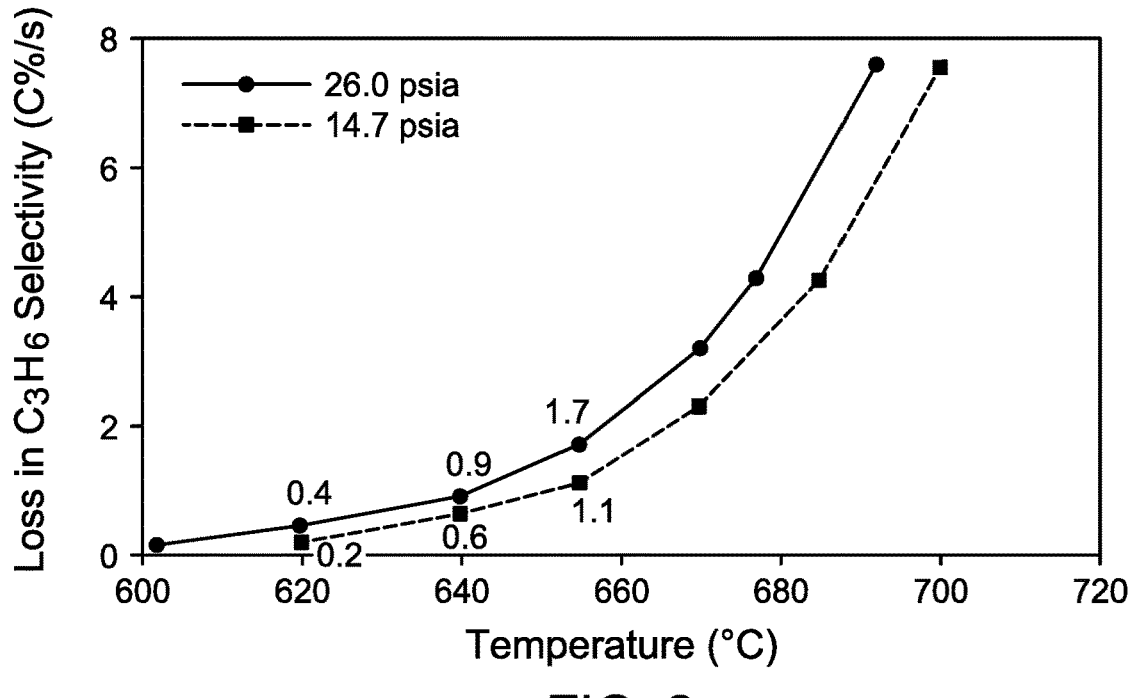
FIG. 2 is a graph illustrating loss in propylene selectivity per second due to secondary thermal cracking at different temperatures.

Experiments were performed to study the effect of secondary thermal and catalytic reactions on propylene ($C_3H_6$ yield) in a lab fixed bed reactor. Experiments were performed in a tube reactor without catalyst loading to measure loss in yields due to secondary thermal cracking. FIG. 1 is a graph illustrating a loss in propylene yield due to secondary thermal cracking per post reactor residence time at the temperature of the reactor outlet at two different pressures. For example, post reactor residence time of 5 seconds at 640° C. at 26 psia will lead to a propylene yield loss of 2.5 carbon mole %. FIG. 2 is a graph illustrating a loss in propylene selectivity due to secondary thermal cracking per post reactor residence time at the temperature of the reactor outlet at two different pressures. This yield and selectivity loss can be attributed to secondary thermal cracking reactions of unconverted propane to non-propylene products and thermal cracking reactions of propylene itself. This yield and selectivity loss can have significant impact on overall economics of propylene production.

Figure 3:
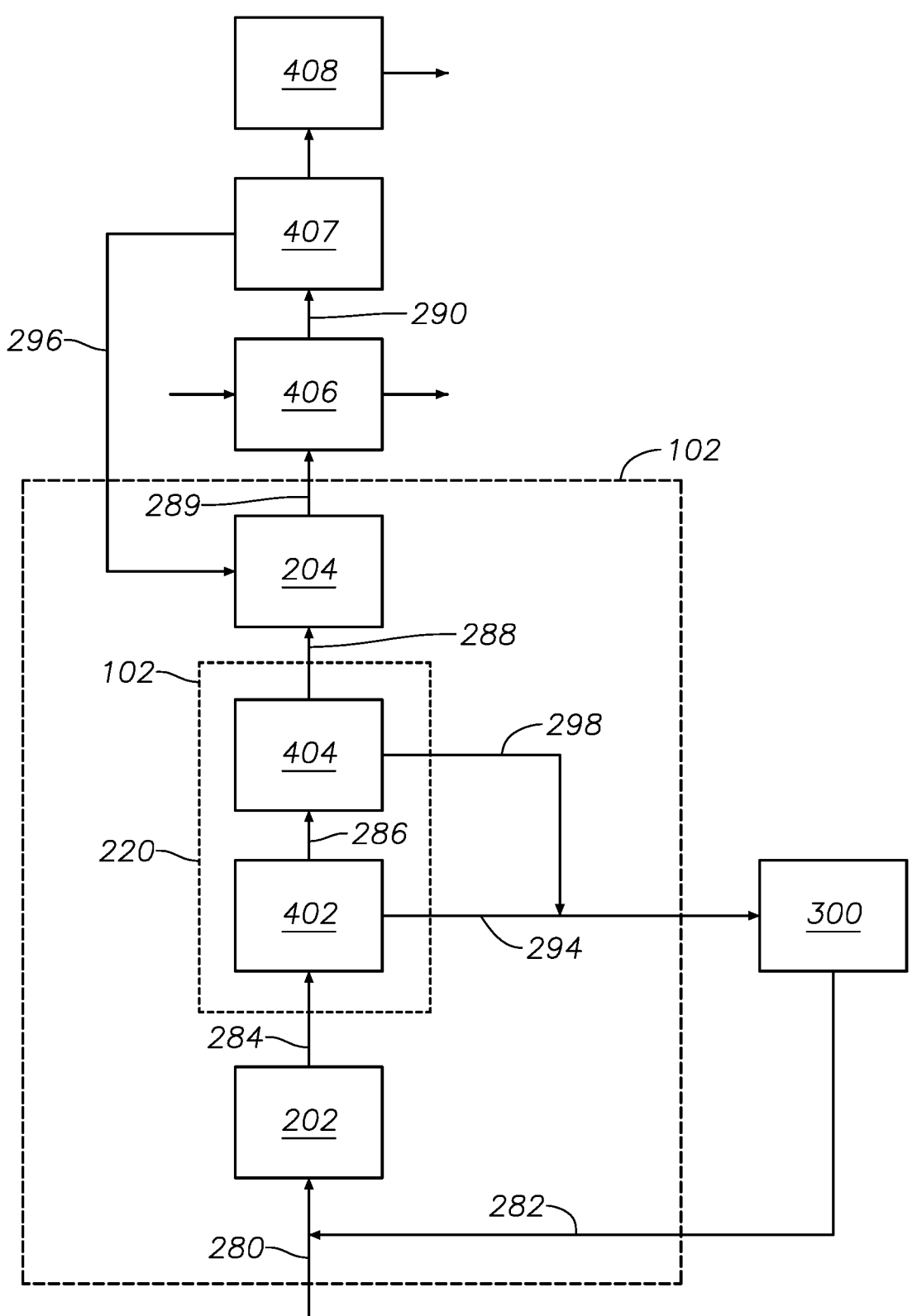
FIG. 3 illustrates an exemplary embodiment of a generalized flow diagram of a reactor system having a recycled quench stream.

FIG. 3 illustrates an exemplary embodiment of a generalized flow diagram of a reactor system having a recycled quench stream. It is noted that many process and equipment details of one or more embodiments of the system of FIG. 3 are described herein with reference to FIG. 4.

Still referring to FIG. 3, the reactor system 102 may include a reactor 202, a separation device 220, and a plenum section 204. The reactor system is coupled with a catalyst processing portion 300. Generally, the main reaction, such as a dehydrogenation reaction, takes place in the reactor 202, where reactant stream 280 (sometimes referred to herein as a hydrocarbon feed stream) from outside of the depicted system is combined with regenerated catalyst of stream 282 from the catalyst processing portion and passed into the reactor 202. Following the reaction, the catalyst, unreacted chemicals, and product chemicals are transferred via stream 284 to the separation device 220. It should be understood that a "product stream" may include both reaction products and unreacted components from reactant stream 280. Reactant stream 280 may comprise one or more of propane, n-butane, iso-butane, ethane, or ethylbenzene.

Stream 284 is referred to sometimes herein as a high temperature dehydrogenated product. Generally, stream 284 has a temperature near that of equal to the temperature at the outlet of the reactor 202. The temperature may depend upon the reaction and utilized catalyst system. In one or more embodiments, stream 284 has a temperature of ranging from 600° C. to 700° C. for propane dehydrogenation, and a pressure ranging from 1.0 bara to 4.0 bara.

The separation device 220 may include a primary separation device 402 and a secondary separation device 404. In additional embodiments, the primary separation device 402 and/or secondary separation device 404 may be, without limitation, cyclones, filters, or other suitable devices for separating solids, such as catalyst, from gases. Following the separation of at least a portion (usually the majority) of the catalyst of stream 284 from the gas phase reactant and product chemicals in the primary separation device 402, the catalyst is passed via stream 294 to the catalyst processing portion 300 and the product and reactant gases (still sometimes referred to as a high temperature dehydrogenated product) may be passed out of the primary separation device 402 via stream 286. The temperature of stream 286 may be about equivalent to that of stream 284.

Following the exit of high temperature dehydrogenation product 286 from the primary separation device 402, product 286 is passed to the secondary separation device 404. The catalyst can be passed via stream 298 to the catalyst processing portion 300. There is no quench fluid applied to the output of the primary separation device 402. The first and secondary separation devices can operate at temperature ranging from 600° C. to 700° C., with a pressure ranging from 1 bara to 4 bara.

Following the exit of high temperature dehydrogenation product via stream 288 from the secondary separation device, the high temperature dehydrogenation product (or, the reactor effluent) is combined with a quench stream 296 in the plenum section 204 of the reactor system 102 to cool the high temperature dehydrogenation product and form stream 289 (sometimes referred to as the intermediate temperature dehydrogenation product). The intermediate temperature dehydrogenation product, preferably, has a temperature no greater than 620° C. The quench stream may be a gas or liquid stream that is a portion of stream 288 that can be separated in a downstream separation system, which is explained in detail herein, or a stream provided from an external source. The quench stream may include one or more of ethylene, propylene, butene isomer or benzene (e.g., the reaction products). The quench stream can include a liquid hydrocarbon and the intermediate temperature product can be completely in a vapor phase.

For example, the quench fluid 296 may include steam, liquid water, liquid hydrocarbon (e.g., a quench oil, fuel oil, or other hydrocarbon), or combinations of these. The liquid hydrocarbon may include hydrocarbons having greater than or equal to 6 carbon atoms, such as from 6 carbon atoms to 25 carbon atoms, or from 6 carbon atoms to 20 carbon atoms. In some embodiments, the quench fluid 296 may include water. Alternatively, in other embodiments, the quench fluid 296 may include liquid hydrocarbon. In still other embodiments, the quench fluid 296 may include one or more than one of benzene, toluene, pyrolysis gas, or combinations of these. The quench stream can include aromatics that are not formed in the high temperature dehydrogenated product. The quench can comprise kerosene, light coker gas oil, coke still (coker) distillates (CSD), hydrotreated distillate, or fresh unprocessed virgin feedstocks, such as virgin gas oil, heavy virgin naphtha, light virgin naphtha, but preferably comprises heavy aromatic solvents like light catalytic cycle oil (LCCO or LCO), heavy catalytic cycle oil (HCCO or HCO), or heavy catalytic naphtha (HCN), aromatic 100 (A100) solvent, aromatic 150 (A150) solvent, aromatic 200 (A200) solvent or any combination thereof.

The quench fluid 296 can lower the temperature of stream 289 to about 620° C. to 580° C., with stream 289 experiencing a pressure change of less than or equal to 0.1 bar due to vaporization.

The temperature of the quench fluid 296 may be less than the temperature of the intermediate stream and catalyst in the stream 288 by greater than or equal to 100° C., greater than or equal to 200° C., greater than or equal to 300° C., greater than or equal to 400° C., or greater than or equal to 550° C. The temperature of the quench stream and the location of the nozzle injecting the quench stream can be optimized as needed to sufficiently slow or stop the secondary thermal and catalytic reactions discussed above.

Stream 289 is then processed to cool its contents via, for example, heat exchanger 406. In additional embodiments, the cooling may include the addition of another liquid quenching system 408 or other known means of cooling a stream. This other quenching system 408 can use any quench fluid described above. Generally, a heat transfer system may include one or both of heat exchanger 406 and other quenching system 408 (or optionally any other means of cooling the stream). The product stream of the heat exchanger 406 is stream 290, which may be referred to as a cooled dehydrogenation product. The temperature of stream 290 may be about the same as that described with respect to the quench stream 296. It should be understood that stream 290 and or stream 296 may be subjected to pressure increase such that they flow in the desired direction.

To form the quench stream 296, at least a portion of stream 290 is recycled back into the system via separation unit 407 (which can be any suitable type of separation means or means for diverting a portion of the stream). It should be noted that the chemical contents of stream 296 may be similar or identical to those of stream 286 (i.e., no further reactions outside of some residual thermal cracking have taken place since those in reactor 202). The quenching of stream 288 by contacting it with the quench stream 296 may cool the contents of stream 286 to a temperature which substantially reduces the reaction rate of thermal cracking and other secondary reactions. Stream 286 may be at a temperature where thermal cracking occurs and such thermal cracking may reduce selectivity of the desired reaction products.

Heat exchanger 406 can be configured to heat feed stream 280 through heat transfer from product stream 289.

According to one or more embodiments, the catalyst particles separated by the separation device 220 and/or catalyst particles recovered from stream 289 (not shown) may be processed by one or more steps before being passed to the catalyst processing portion 300.

FIG. 4 illustrates an exemplary reactor embodying the present technological advancement. The reactor design illustrated in FIG. 4 minimizes the secondary reactions discussed above. In this configuration, the propane feed comes in contact with dehydrogenation catalyst in the riser section of the reactor at high temperature (>600° C.). The dehydrogenation catalyst is separated from the high temperature product stream in primary and secondary separators. The resultant high temperature product stream includes dehydrogenation product (propylene), byproducts (methane, benzene, etc.) and unconverted propane. This stream output from the secondary separator is immediately quenched with a liquid quench stream. The liquid quench stream can include byproducts of the dehydrogenation reaction (benzene) or other external fluids (water or A150). The quench liquid vaporizes in contact with the high temperature stream in the plenum section of the reactor. The direct heat transfer results in reduction in temperature of the product stream and rate of secondary reactions.

While FIG. 4 is described in connection with a propylene/propane embodiment, the present technical advancement can be applied to the production of other olefins. Also, while in some cases like numbers are utilized in FIG. 4 with respect to FIG. 3, it should be understood that the embodiments of FIG. 3 may utilize a wide variety of reactor types and that FIG. 4 is only an example of one such type.

FIG. 4 illustrates an embodiment of a portion of the reactor system 102 of FIG. 3, referred to sometimes as the reactor vessel 410 wherein the separation device includes a primary separation device 420. The primary separation device 420 is contained within a shell 430 and has a body 421, an inlet 422, an outlet 424 and a solids discharge dipleg 426. A fluidized solid stream enters the primary separation device 420 through inlet 422. In the primary separation device 420, a major part of entrained solids, e.g. catalyst particles, are separated from the fluidized solid stream. The separated solids exit the primary separation device through discharge dipleg 426 leaving a primary separation device effluent which comprises solids not removed by the primary separation device 420 and fluid, e.g. gaseous product. The primary separation device effluent passes vertically upward and out of the primary separation device 420 through outlet 424 and into the secondary separation device 440 through primary separation device outlet tube 442 and then through crossover duct (not shown). The secondary separation device 440 further comprises a body 441, an outlet 444 and a solids discharge dipleg 446. The secondary separation device 440 further separates out solids from the primary separation device effluent. Solids separated out in the secondary separation device 440 exit downward through dipleg 446.

As depicted in FIG. 4, quench stream 296 may enter the upper portion of the secondary separation device outlet tube 444, which is positioned above the secondary separation device 440. It is believed that such an arrangement may be desirable for proper mixing of the quench stream with the effluent of the secondary separation device 440 and to reduce residence time between the exit of the secondary separation device 440 and the location of the inlet or nozzle for the quench stream 296. In some embodiments, the residence time of the high temperature dehydrogenation product in each of the primary separation device and the secondary separation device is less than one second.

Secondary separation device outlet 444 is fluidly connected to a second plenum 450. Second plenum allows the secondary separation device effluent to pass out of the vessel 410 through outlet 470. As shown in FIG. 4, the second plenum is housed within a larger, higher volume first plenum 460. Primary separation device 420 may be supported by the first plenum 460.

The exact location of the inlet or nozzle for the quench stream 296 may vary depending the actual reactor being used, but it can be disposed at a location within the first plenum 460 or second plenum 450 that minimizes secondary catalytic cracking within the high temperature dehydrogenation product and/or minimizes yield loss of the olefin (i.e., propylene) within the high temperature dehydrogenation product (note, that pipe, duct, or conduit for 296 in the secondary plenum is partially shown in a dashed line as that portion would be behind metal plate defining second plenum 450). Preferably, the quench stream 296 can be configured to minimize the needed piping so that all secondary separation devices can be quenched by a single inlet or nozzle; thus quenching in the area of the second plenum 450 in order to provide a simplified reactor design. Thus, while FIG. 4 illustrates two possible locations for the inlet or nozzle for quench stream 296, one or both could be used in practice. However, it is important to note that no quench stream is provided to an output region (i.e., output 424) of the primary separator 420.

Also shown in FIG. 4, the shell 430 further houses a riser 435. An unseparated stream of fluidized solid particles enters the shell through riser 435. Riser 435 fluidly connects, i.e. allows passage of the fluidized solid particles, with the inlet 422 of the primary separation device 420 such that the unseparated stream of fluidized solid particles may pass from the riser 435 into primary separation device 420. It will be understood that while FIG. 4 schematically illustrates only one primary separation device and one secondary separation device, additional primary and secondary separation devices may be placed around the periphery of the riser. For example, second plenum 450 could be connected to another secondary separation device (not shown) which in turn is fed either by primary separation device 420 or by another primary separation device (not shown).

Experiment to Demonstrate Catalyst Stability

Those of ordinary skill in the art will recognize that any suitable catalyst for their purpose could be used in a reactor embodying the present technological advancement. In some embodiments, the catalyst can include 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.015 wt %, 0.02 wt %, 0.025 wt %, 0.03 wt %, 0.035 wt %, 0.04 wt %, 0.045 wt %, 0.05 wt %, 0.055 wt %, 0.06 wt %, 0.065 wt %, 0.07 wt %, 0.075 wt %, 0.08 wt %, 0.085 wt %, 0.09 wt %, 0.095 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, 5 wt %, or 6 wt % of a Group 10 element disposed on an inorganic support, based on the weight of the inorganic support. In some embodiments, the catalyst can include ≤5.5 wt %, ≤4.5 wt %, ≤3.5 wt %, ≤2.5 wt %, ≤1.5 wt %, ≤1 wt %, ≤0.9 wt %, ≤0.8 wt %, ≤0.7 wt %, ≤0.6 wt %, ≤0.5 wt %, ≤0.4 wt %, ≤0.3 wt %, ≤0.2 wt %, ≤0.15 wt %, ≤0.1 wt %, ≤0.09 wt %, ≤0.08 wt %, ≤0.07 wt %, ≤0.06 wt %, ≤0.05 wt %, ≤0.04 wt %, ≤0.03 wt %, ≤0.02 wt %, ≤0.01 wt %, ≤0.009 wt %, ≤0.008 wt %, ≤0.007 wt %, ≤0.006 wt %, ≤0.005 wt %, ≤0.004 wt %, ≤0.003 wt %, or ≤0.002 wt % of the Group 10 element disposed on the inorganic support, based on the weight of the inorganic support. In some embodiments, the catalyst can include >0.001, >0.003 wt %, >0.005 wt %, >0.007, >0.009 wt %, >0.01 wt %, >0.02 wt %, >0.04 wt %, >0.06 wt %, >0.08 wt %, >0.1 wt %, >0.13 wt %, >0.15 wt %, >0.17 wt %, >0.2 wt %, >0.2 wt %, >0.23, >0.25 wt %, >0.27 wt %, or >0.3 wt % and <0.5 wt %, <1 wt %, <2 wt %, <3 wt %, <4 wt %, <5 wt %, or <6 wt % of the Group 10 element disposed on the inorganic support, based on the weight of the inorganic support.

In some embodiments, the Group 10 element can be or can include Ni, Pd, Pt, a combination thereof, or a mixture thereof. In at least one embodiment, the Group 10 element can be or can include Pt. If two or more Group 10 elements are disposed on the inorganic support, the catalyst can include 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.015 wt %, 0.02 wt %, 0.025 wt %, 0.03 wt %, 0.035 wt %, 0.04 wt %, 0.045 wt %, 0.05 wt %, 0.055 wt %, 0.06 wt %, 0.065 wt %, 0.07 wt %, 0.075 wt %, 0.08 wt %, 0.085 wt %, 0.09 wt %, 0.095 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, 5 wt %, or 6 wt % of a combined amount of the two or more Group 10 elements disposed on the inorganic support, based on the weight of the inorganic support. In some embodiments, an active component of the regenerated catalyst that can be capable of effecting dehydrogenation of the hydrocarbon feed stream can include the group 10 element.

The inorganic support can be or can include, but is not limited to, one or more Group 2 elements, a combination thereof, or a mixture thereof. In some embodiments, the Group 2 element can be present in its elemental form. In other embodiments, the Group 2 element can be present in the form of a compound. For example, the Group 2 element can be present as an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide. In some embodiments, a mixture of any two or more compounds that include the Group 2 element can be present in different forms. For example, a first compound can be an oxide and a second compound can be an aluminate where the first compound and the second compound include the same or different Group 2 element, with respect to one another.

The inorganic support can include ≥0.5 wt %, ≥1 wt %, ≥2 wt %, ≥3 wt %, ≥4 wt %, ≥5 wt %, ≥6 wt %, ≥7 wt %, ≥8 wt %, ≥9 wt %, ≥10 wt %, ≥11 wt %, ≥12 wt %, ≥13 wt %, ≥14 wt %, ≥15 wt %, ≥16 wt %, ≥17 wt %, ≥18 wt %, ≥19 wt %, ≥20 wt %, ≥21 wt %, ≥22 wt %, ≥23 wt %, ≥24 wt %, ≥25 wt %, ≥26 wt %, ≥27 wt %, ≥28 wt %, ≥29 wt %, ≥30 wt %, ≥35 wt %, ≥40 wt %, >45 wt %, ≥50 wt %, ≥55 wt %, ≥60 wt %, ≥65 wt %, ≥70 wt %, ≥75 wt %, ≥80 wt %, ≥85 wt %, or ≥90 wt % of the Group 2 element, based on the weight of the inorganic support. In some embodiments, the inorganic support can include the Group 2 element in a range of from 0.5 wt %, 1 wt %, 2 wt %, 2.5 wt %, 3 wt %, 5 wt %, 7 wt %, 10 wt %, 11 wt %, 13 wt %, 15 wt %, 17 wt %, 19 wt %, 21 wt %, 23 wt %, or 25 wt % to 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, or 92.34 wt % based on the weight of the inorganic support. In some embodiments, a molar ratio of the Group 2 element to the Group 10 element can be in a range from 0.24, 0.5, 1, 10, 50, 100, 300, 450, 600, 800, 1,000, 1,200, 1,500, 1,700, or 2,000 to 3,000, 3,500, 4,000, 4,500, 5,000, 5,500, 6,000, 6,500, 7,000, 7,500, 8,000, 8,500, 9,000, 9,500, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 200,000, 300,000, 400,000, 500,000, 600,000, 700,000, 800,000, or 900,000.

In some embodiments, the inorganic support can include the Group 2 element and Al and can be in the form of a mixed Group 2 element/Al metal oxide that has O, Mg, and Al atoms mixed on an atomic scale. In some embodiments the inorganic support can be or can include the Group 2 element and Al in the form of an oxide or one or more oxides of the Group 2 element and $Al_2O_3$ that can be mixed on a nm scale. In some embodiments, the inorganic support can be or can include an oxide of the Group 2 element, e.g., MgO, and $Al_2O_3$ mixed on a nm scale.

In some embodiments, the inorganic support can be or can include a first quantity of the Group 2 element and Al in the form of a mixed Group 2 element/Al metal oxide and a second quantity of the Group 2 element in the form of an oxide of the Group 2 element. In such embodiment, the mixed Group 2 element/Al metal oxide and the oxide of the Group 2 element can be mixed on the nm scale and the Group 2 element and Al in the mixed Group 2 element/Al metal oxide can be mixed on the atomic scale.

In other embodiments, the inorganic support can be or can include a first quantity of the Group 2 element and a first quantity of Al in the form of a mixed Group 2 element/Al metal oxide, a second quantity of the Group 2 element in the form of an oxide of the Group 2 element, and a second quantity of Al in the form of $Al_2O_3$. In such embodiment, the mixed Group 2 element/Al metal oxide, the oxide of the Group 2 element, and the $Al_2O_3$ can be mixed on a nm scale and the Group 2 element and Al in the mixed Group 2 element/Al metal oxide can be mixed on the atomic scale.

In some embodiments, when the inorganic support includes the Group 2 element and Al, a weight ratio of the Group 2 element to the Al in the inorganic support can be in a range from 0.001, 0.005, 0.01, 0.05, 0.1, 0.15, 0.2, 0.3, 0.5, 0.7, or 1 to 3, 6, 12.5, 25, 50, 75, 100, 200, 300, 400, 500, 600, 700, 800, 900, or 1,000. In some embodiments, when the inorganic support includes Al, the inorganic support can include Al in a range from 0.5 wt %, 1 wt %, 1.5 wt %, 2 wt %, 2.1 wt %, 2.3 wt %, 2.5 wt %, 2.7 wt %, 3 wt %, 4 wt %, 5 wt %, 6 wt %, 7 wt %, 8 wt %, 9 wt %, 10 wt %, or 11 wt % to 15 wt %, 20 wt %, 25 wt %, 30 wt %, 40 wt %, 45 wt %, or 50 wt %, based on the weight of the inorganic support.

In some embodiments, the catalyst can be made by depositing Pt and Sn onto a support that contains at least one alkaline earth metal oxide or at least one mixed metal oxide that contains at least one alkaline earth metal. The composition of the catalyst can be as follows: Pt 0.001 wt % to 6 wt % based on a weight of the support; Sn 0 wt % to 10 wt % based on the weight of the support; the support includes at least one alkaline earth metal oxide. The total alkaline earth metal content can be at least 0.5 wt % based on the weight of the support. The catalyst can be of Geldart A or B type according to the Geldart Classification of Particles.

Other catalysts can be used, and may be at least partially deactivated at some point in the implementation of the method and/or system. The catalyst can include a Group 10 element, an inorganic support, and a contaminant, where the Group 10 element has a concentration in the range of from 0.001 wt % to 6 wt %, based on the weight of the inorganic support. The Group 10 element can be or can include Pt, and where the inorganic support includes at least 0.5 wt % of a Group 2 element, based on weight of the inorganic support. The Group 2 element can include Mg, and at least a portion of the Group 2 element can be in a form of MgO or a mixed metal oxide that includes Mg. The catalyst can further include up to 10 wt % of a promoter, based on weight of the inorganic support, and where the promoter can include one or more of the following elements: Sn, Ag, Cu, a combination thereof, or a mixture thereof. The catalyst can further include up to 5 wt % an alkali metal element disposed on the inorganic support, where the alkali metal element can include at least one of: Li, Na, K, Rb, and Cs. Further examples of catalysts usable with the present technological advancement can be found in Application Ser. No. 63/195, 966, file Jun. 2, 2021, the entirety of which is hereby incorporated by reference.

Catalyst 1: An Mg/Al oxide support was prepared by spray-drying an aqueous slurry containing calcined Mg/Al hydrotalcite PURALOX® MG 70/170 (Sasol) and aluminum chlorohydrate (ACH). The final support after calcination contained 80 wt % calcined hydrotalcite and 20 wt % alumina derived from ACH. An aqueous solution of tin (IV) chloride pentahydrate (Acros Organics) and chloroplatinic acid hexahydrate (BioXtra) was impregnated onto the support. The impregnated material was kept at room temperature in a closed container for 45 hours, before it was dried at 110° C. for 6 hours, and calcined at 800° C. for 12 hours, all in air. The final product contained nominally 0.3 wt % Pt and 1.5 wt % Sn.

Fixed bed experiments were conducted at approximately 100 kPa-absolute, unless otherwise specified. A gas chromatograph (GC) was used to measure the composition of the reactor effluents. The concentrations of each component in the reactor effluents were then used to calculate the $C_3H_6$ yield and selectivity. The $C_3H_6$ yield and selectivity, as reported in these examples, were calculated on the carbon mole basis.

In each example, a certain amount of the catalyst "Mcat" was mixed with an appropriate amount of quartz diluent and loaded into a quartz reactor. The amount of diluent was determined so that the catalyst bed (catalyst+diluent) overlapped with the isothermal zone of the quartz reactor and the catalyst bed was largely isothermal during operation. The dead volume of the reactor was filled with quartz chips/rods.

The concentration of each component in the reactor effluent was used to calculate the $C_3H_6$ yield and selectivity. The $C_3H_6$ yield and the selectivity at the beginning of $t_{rxn}$ and at the end of $t_{rxn}$ is denoted as $Y_{ini}$, $Y_{end}$, $S_{ini}$, and $S_{end}$, respectively, and reported as percentages in the data tables below.

Example 1

1. The system was flushed with an inert gas. 2. An oxygen containing gas ($O_{gas}$) at a flow rate ($F_{oxi}$) was passed through the by-pass of the reaction zone, while an inert was passed through the reaction zone. The reaction zone was heated to an oxidation temperature $T_{oxi}$. 3. The oxygen containing gas was then passed through the reaction zone for a certain period of time ($t_{oxi}$) to oxidize the catalyst. After $t_{oxi}$, the temperature within the reaction zone was changed from $T_{oxi}$ to a reduction temperature ($T_{red}$) while maintaining the oxygen-containing gas flow. 4. The system was flushed with an inert gas. 5. A H$_2$ containing gas (H$_{gas}$) at a flow rate (F$_{red}$) was passed through the by-pass of the reaction zone for a certain period of time, while an inert was passed through the reaction zone. This was then followed by flowing the H$_2$ containing gas through the reaction zone at T$_{red}$ for a certain period of time (t$_{red}$). 6. The system was flushed with an inert. During this process, the temperature of the reaction zone was changed from T$_{red}$ to a reaction temperature of 655° C. 7. A hydrocarbon-containing (HC-gas) feed that included 81 vol % of C$_3$H$_8$, 9 vol % of inert (Ar or Kr) and 10 vol % of steam at a flow rate (F$_{rxn}$) was passed through the by-pass of the reaction zone for a certain period of time, while an inert was passed through the reaction zone. The hydrocarbon-containing feed was then passed through the reaction zone at 655° C. for 10 minutes. GC sampling of the reaction effluent started as soon as the feed was switched from the by-pass of the reaction zone to the reaction zone.

Figure 5:
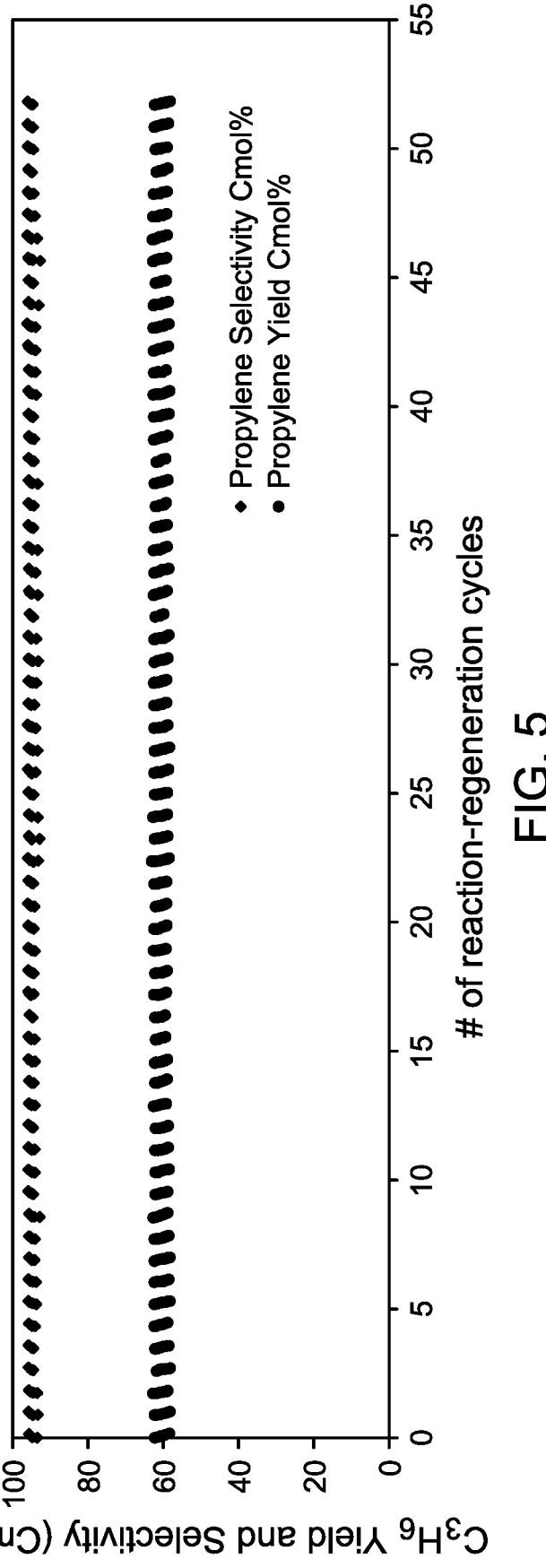
FIG. 5 is a graph illustrating PDH performance of a typical PDH catalyst relevant to the present technological advancement.

The above process steps were repeated in cycles until stable performance was obtained. Table 1 shows that Catalyst 1 was active/selective for propane dehydrogenation and can be effectively regenerated by using such a two-step oxidation scheme for 60+ cycles. FIG. 5 shows that catalyst 1 was stable over 60 cycles for propane dehydrogenation.

TABLE 1

| Catalyst | | 1 |
|---|---|---|
| M$_{cat}$ (g) | | 0.3 |
| F$_{rxn}$ (sccm) | | 17.6 |
| Hgas | | 10% H$_2$ |
| | | 90% Ar |
| F$_{red}$ (sccm) | | 46.6 |
| T$_{red}$ (° C.) | | 800 |
| t$_{red}$ (min) | | 0.05 |
| Ogas | | 90% Air |
| | | 10% H$_2$O |
| | | Then |
| | | Dry air |
| F$_{oxi}$ (sccm) | | 93.2 |
| | | Then |
| | | 83.9 |
| T$_{oxi}$ (° C.) | | 800 |
| t$_{oxi}$ (min) | | 1 |
| | | Then |
| | | 10 |
| Performance | Y$_{ini}$ | 62.4 |
| | Y$_{end}$ | 59.8 |
| | S$_{ini}$ | 94.5 |
| | S$_{end}$ | 96.1 |

Example 2

A simulated propane dehydrogenation product was fed into a reaction zone packed with inert quartz chips to study its thermal cracking under different temperatures and pressures. The molar composition of the simulated propane dehydrogenation product is shown in Table 2.

TABLE 2

| Component | Molar % |
|---|---|
| H$_2$ | 38.0 |
| Ar | 6.0 |
| CH$_4$ | 1.32 |
| CO | 0.80 |
| C$_3$H$_8$ | 18.0 |
| C$_3$H$_6$ | 34.2 |
| CO$_2$ | 0.30 |

TABLE 2-continued

| Component | Molar % |
|---|---|
| C$_2$H$_4$ | 0.49 |
| C$_2$H$_6$ | 0.80 |

The simulated propane dehydrogenation product corresponds to a propylene yield and selectivity of 63.7% and 95.5%, respectively.

When passed through the reactor, the components of the simulated propane dehydrogenation product further cracked. The rate of cracking was calculated under differential conversions and was expressed as the losses in propylene yield and selectivity per second. FIG. 1 is a graph illustrating loss in propylene yield per second at different temperatures (x-axis being temperature in degree Celsius and the y-axis being %). FIG. 2 is a graph illustrating the loss in propylene selectivity per second at different temperatures (x-axis being temperature in degree Celsius and the y-axis being %).

The above experiments were also conducted with ~5 mol % to 10 mol % of steam co-fed with the simulated propane dehydrogenation product. It was found that the small amount of steam had minimal impacts to the rate of cracking. The minimal impacts to the rate of cracking can be attributed to the lower hydrocarbon partial pressure due to the presence of steam.

Example 3

The following experiments were conducted in order to understand the reaction of a propane dehydrogenation product entrained with catalyst not separated by the cyclonic device when the propane dehydrogenation product entrained with catalyst flows through equipment downstream of the cyclonic devices at various temperatures.

Feed A, consisting of a simulated propane dehydrogenation product and an appropriate amount of steam, was fed into a reaction zone packed with inert quartz chips and various amounts of Catalyst 2 to study hydrogenation, thermal cracking and catalytic cracking of Feed A under different temperatures. Catalyst 2 was prepared according to the following procedure: Set aside 2.3 g PURALOX® MG 70/170 (Sasol), which was a MgO—Al$_2$O$_3$ mixed metal oxide obtained by calcining hydrotalcite. The mixed metal oxide contained 70 wt % MgO and 30 wt % Al$_2$O$_3$. The BET surface area was 170 m$^2$/g according to Sasol. Tin (IV) chloride pentahydrate (0.103 g) (Acros Organics), chloroplatinic acid hexahydrate (0.0184 g) (BioXtra), and deionized water (2.2 mL) were mixed in a small glass vial to make a solution. The PURALOX® MG 70/170 support was impregnated with the solution. The impregnated material was dried at 110° C. for 6 hours, and calcined at 800° C. for 12 hours, all in air. The final product contained nominally 0.3 wt % Pt and 1.5 wt % Sn.

The molar composition of Feed A is shown in Table 3.

TABLE 3

| Component | Molar % |
|---|---|
| H$_2$ | 33.8 |
| Ar | 5.3 |
| CH$_4$ | 1.2 |
| CO | 0.7 |
| C$_3$H$_8$ | 16.0 |
| C$_3$H$_6$ | 30.5 |
| CO$_2$ | 0.3 |

TABLE 3-continued

| Component | Molar % |
|-----------|---------|
| $C_2H_4$ | 0.4 |
| $C_2H_6$ | 0.7 |
| Steam | 11.0 |

Feed A corresponds to a simulated propane dehydrogenation product with propylene yield and selectivity of 63.7% and 95.5%, respectively.

The total pressure of Feed A was ~100 kPa-absolute. The flow rate of Feed A and the amount of Catalyst 2 in the reaction zone was varied so that the weight hourly space velocity (WHSV), calculated by dividing the mass flow rate of the C-containing components in Feed A by the weight of Catalyst 2 in the reaction zone was varied from 121 $h^{-31}$, 350 $h^{-1}$ and infinite (no catalyst).

The flow rate of Feed A was also varied so that the thermal residence time of Feed A in the reaction zone, calculated by dividing the void volume of the reaction zone by the volumetric flow rate of Feed A at reaction temperature/pressure, was 2 seconds. The reaction zone was largely isothermal. The temperature dropped rapidly outside of the reaction zone.

When passing through the reaction zone, Feed A may further crack (thermal or catalytic), dehydrogenate or hydrogenate to form Product A. The propylene yield and selectivity of Feed A, 63.7% and 95.5%, may change after reaction. For example, if hydrogenation of propylene occurs in the reaction zone, then the propylene yield of Product A decreases.

Figure 6:
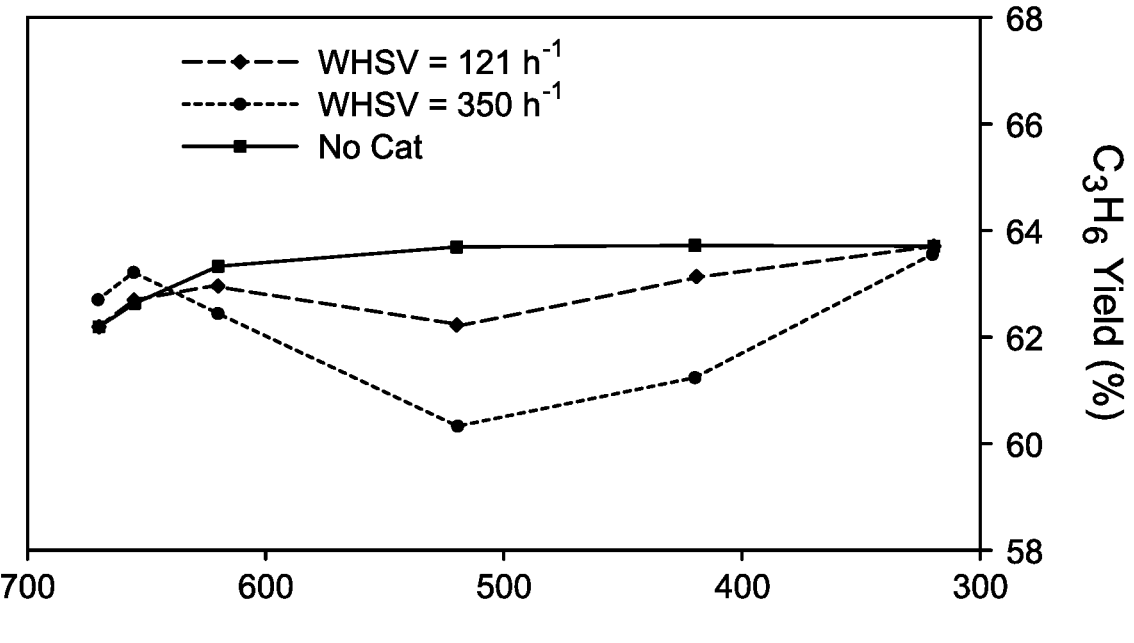
FIG. 6 is a graph illustrating the $C_3H_6$ yield of Product A vs reaction zone temperature.

FIG. 6 (x-axis temperature in Celsius; y-axis propylene yield (%)) shows the propylene yield of Product A vs. reaction zone temperature when the thermal residence time was kept at 2 seconds. The WHSV was varied from 121 $h^{-1}$ (orange, line (b)), 350 $h^{-1}$ (blue, line (a)), and infinite (no catalyst) (gray, line (c)). When there was no catalyst, the propylene yield loss at T>600° C. was entirely due to thermal cracking of propylene. When catalyst was present, a large amount of loss in propylene yield was seen at T<600° C., primarily due to the hydrogenation of propylene. The extent of hydrogenation reaction reduces quickly when the WHSV increases, i.e. when the amount of catalysts not separated by the cyclonic device reduces in the propane dehydrogenation product. The propylene yield loss due hydrogenation was largest at T~500° C.

Figure 7:
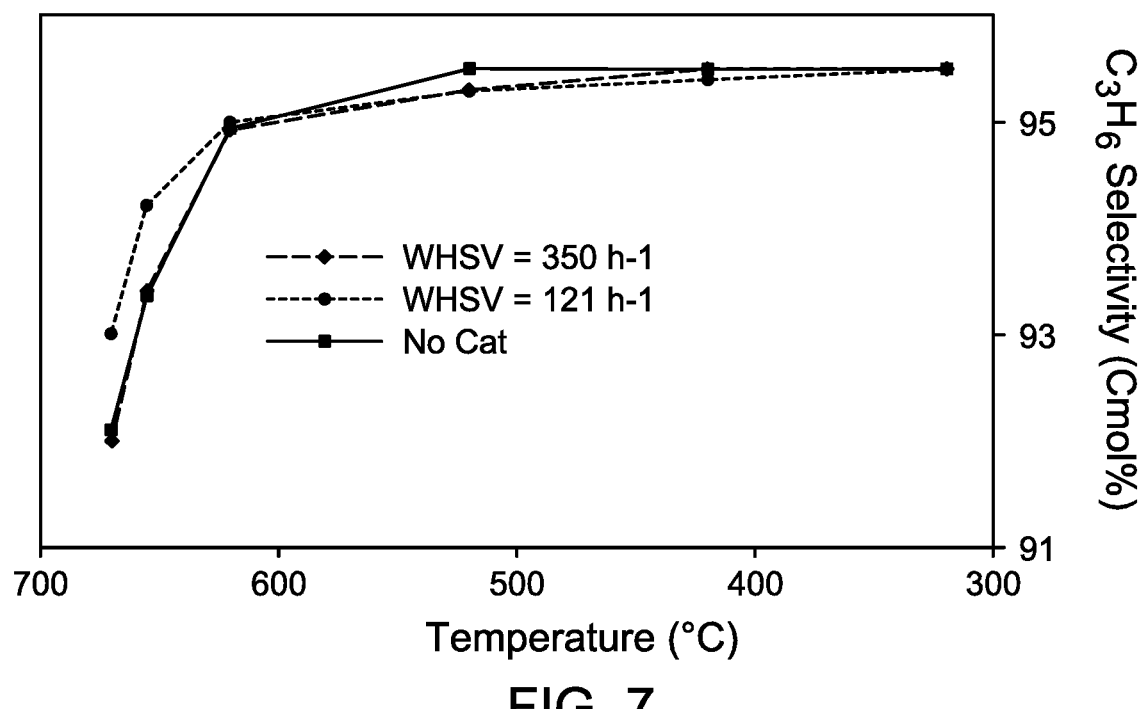
FIG. 7 is graph illustrating the $C_3H_6$ selectivity of Product A vs reaction zone temperature.

FIG. 7 shows the propylene selectivity of Product A vs. reaction zone temperature when the thermal residence time was kept at 2 s. The WHSV was varied from 121 $h^{-1}$ (orange, line (b)), 350 $h^{-1}$ (blue, line (a)), and infinite (no catalyst) (gray, line (c)). When there was no catalyst, the propylene selectivity loss at T>600° C. was entirely due to thermal cracking of propylene. Interestingly, the propylene selectivity was higher when WHSV was 121 $h^{-1}$. This may be due to the suppression of thermal cracking by Catalyst 2.

FIGS. 6 and 7 show that to avoid hydrogenation of the propylene during quenching. The following tactics may be employed. (1) Reduce the amount of entrained catalysts in the propane dehydrogenation product before quenching the product. (2) Quench the propane dehydrogenation product to <320° C. rapidly since the rate of hydrogenation is slow when T<320° C. (3) Use a quench that reversibly deactivates the entrained catalyst.

Catalyst compositions 3-16 were prepared according to the following procedure. For each catalyst composition PURALOX® MG 80/150 (3 grams) (Sasol), which was a mixed Mg/Al metal oxide that contained 80 wt % of MgO and 20 wt % of $Al_2O_3$ and had a surface area of 150 $m^2/g$, was calcined under air at 550° C. for 3 hours to form a support. Solutions that contained a proper amount of tin (IV) chloride pentahydrate when used to make the catalyst composition (Acros Organics) and/or chloroplatinic acid when used to make the catalyst composition (Sigma Aldrich), and 1.8 ml of deionized water were prepared in small glass vials. The calcined PURALOX® MG 80/150 supports (2.3 grams) for each catalyst composition were impregnated with the corresponding solution. The impregnated materials were allowed to equilibrate in a closed container at room temperature (RT) for 24 hours, dried at 110° C. for 6 hours, and calcined at 800° C. for 12 hours. Table 1 shows the nominal Pt and Sn content of each catalyst composition based on the weight of the support.

TABLE 4

| Catalyst | Pt (wt %) | Sn (wt %) |
|----------|-----------|-----------|
| 3 | 0.4 | 1 |
| 4 | 0.3 | 1 |
| 5 | 0.2 | 1 |
| 6 | 0.1 | 1 |
| 7 | 0.05 | 1 |
| 8 | 0.025 | 1 |
| 9 | 0.0125 | 1 |
| 10 | 0 | 1 |
| 11 | 0.1 | 0.5 |
| 12 | 0.1 | 1 |
| 13 | 0.1 | 2 |
| 14 | 0.0125 | 0 |
| 15 | 0.0125 | 0.5 |
| 16 | 0.0125 | 2 |

Example 4

Fixed bed experiments were conducted at approximately 100 kPa-absolute that used catalysts 3-16. A gas chromatograph (GC) was used to measure the composition of the reactor effluents. The concentrations of each component in the reactor effluents were then used to calculate the $C_3H_6$ yield and selectivity. The $C_3H_6$ yield and selectivity, as reported in these examples, were calculated on the carbon mole basis.

In each example, 0.3 g of the catalyst composition was mixed with an appropriate amount of quartz diluent and loaded into a quartz reactor. The amount of diluent was determined so that the catalyst bed (catalyst+diluent) overlapped with the isothermal zone of the quartz reactor and the catalyst bed was largely isothermal during operation. The dead volume of the reactor was filled with quartz chips/rods.

The $C_3H_6$ yield and the selectivity at the beginning of $t_{ran}$ and at the end of $t_{rxn}$ is denoted as $Y_{ini}$, $Y_{end}$, $S_{ini}$, and $S_{end}$, respectively, and reported as percentages in Tables 5 and 6 below for catalysts 3-10.

The process steps for catalysts 3-10 were as follows: 1. The system was flushed with an inert gas. 2. Dry air at a flow rate of 83.9 sccm was passed through a by-pass of the reaction zone, while an inert was passed through the reaction zone. The reaction zone was heated to a regeneration temperature of 800° C. 3. Dry air at a flow rate of 83.9 sccm was then passed through the reaction zone for 10 min to regenerate the catalyst. 4. The system was flushed with an inert gas. 5. A $H_2$ containing gas with 10 vol % $H_2$ and 90 vol % Ar at a flow rate of 46.6 sccm was passed through the by-pass of the reaction zone for a certain period of time, while an inert gas was passed through the reaction zone. This is then followed by flowing the $H_2$ containing gas through the reaction zone at 800° C. for 3 seconds. 6. The system was flushed with an inert gas. During this process, the temperature of the reaction zone was changed from 800° C. to a reaction temperature of 670° C. 7. A hydrocarbon-containing (HCgas) feed that included 81 vol % of $C_3H_8$, 9 vol % of inert gas (Ar or Kr) and 10 vol % of steam at a flow rate of 35.2 sccm was passed through the by-pass of the reaction zone for a certain period of time, while an inert gas was passed through the reaction zone. The hydrocarbon-containing feed was then passed through the reaction zone at 670° C. for 10 min. GC sampling of the reaction effluent started as soon as the feed was switched from the by-pass of the reaction zone to the reaction zone.

The above process steps were repeated in cycles until stable performance was obtained. Tables 5 and 6 show that Catalyst 8 that contained only 0.025 wt % of Pt and 1 wt % of Sn had both a similar yield and a similar selectivity as compared to Catalyst 3 that contained 0.4 wt % of Pt and 1 wt % of Sn, which was surprising and unexpected. Catalyst 10 that did not include any Pt did not show an appreciable propylene yield.

TABLE 5

|  |  | Catalyst 3 | Catalyst 4 | Catalyst 5 | Catalyst 6 |
|---|---|---|---|---|---|
| Performance | $Y_{ini}$ | 61.7 | 61.7 | 60.7 | 63.7 |
|  | $Y_{end}$ | 55.2 | 55.7 | 54.2 | 56.7 |
|  | $S_{ini}$ | 97.3 | 97.2 | 97.0 | 97.1 |
|  | $S_{end}$ | 98.1 | 98.0 | 97.7 | 98.3 |

TABLE 6

|  |  | Catalyst 7 | Catalyst 8 | Catalyst 9 | Catalyst 10 |
|---|---|---|---|---|---|
| Performance | $Y_{ini}$ | 62.4 | 62.0 | 56.7 | 2.0 |
|  | $Y_{end}$ | 57.2 | 54.6 | 45.7 | 1.7 |
|  | $S_{ini}$ | 96.7 | 97.3 | 96.9 | 64.2 |
|  | $S_{end}$ | 97.7 | 98.0 | 97.6 | 49.5 |

Catalysts 11-16 were also tested using the same process steps 1-7 described above with regard to catalysts 3-10. Table 7 shows that the level of Sn should not be too low or too high for optimal propylene yield for the catalyst compositions that included 0.1 wt % of Pt based on the weight of the support.

TABLE 7

|  |  | Catalyst 11 0.5 wt % Sn | Catalyst 6 1 wt % Sn | Catalyst 12 1 wt % Sn | Catalyst 13 2 wt % Sn |
|---|---|---|---|---|---|
| Performance | $Y_{ini}$ | 58.4 | 63.7 | 63.4 | 56.5 |
|  | $Y_{end}$ | 49.5 | 56.7 | 55.5 | 47.7 |
|  | $S_{ini}$ | 96.9 | 97.1 | 97.2 | 97.8 |
|  | $S_{end}$ | 97.6 | 98.3 | 98.1 | 98.2 |

Table 8 shows that the level of Sn should not be too high or too low for optimal propylene yield for the catalyst compositions that included 0.0125 wt % of Pt based on the weight of the support.

TABLE 8

|  |  | Catalyst 14 0 wt % Sn | Catalyst 15 0.5 wt % Sn | Catalyst 9 1 wt % Sn | Catalyst 16 2 wt % Sn |
|---|---|---|---|---|---|
| Performance | $Y_{ini}$ | 2.6 | 44 | 56.7 | 55.4 |
|  | $Y_{end}$ | 1.7 | 24.4 | 45.7 | 44.1 |
|  | $S_{ini}$ | 63.9 | 96.7 | 96.9 | 96.8 |
|  | $S_{end}$ | 61.1 | 95.6 | 97.6 | 97.6 |

Figure 8:
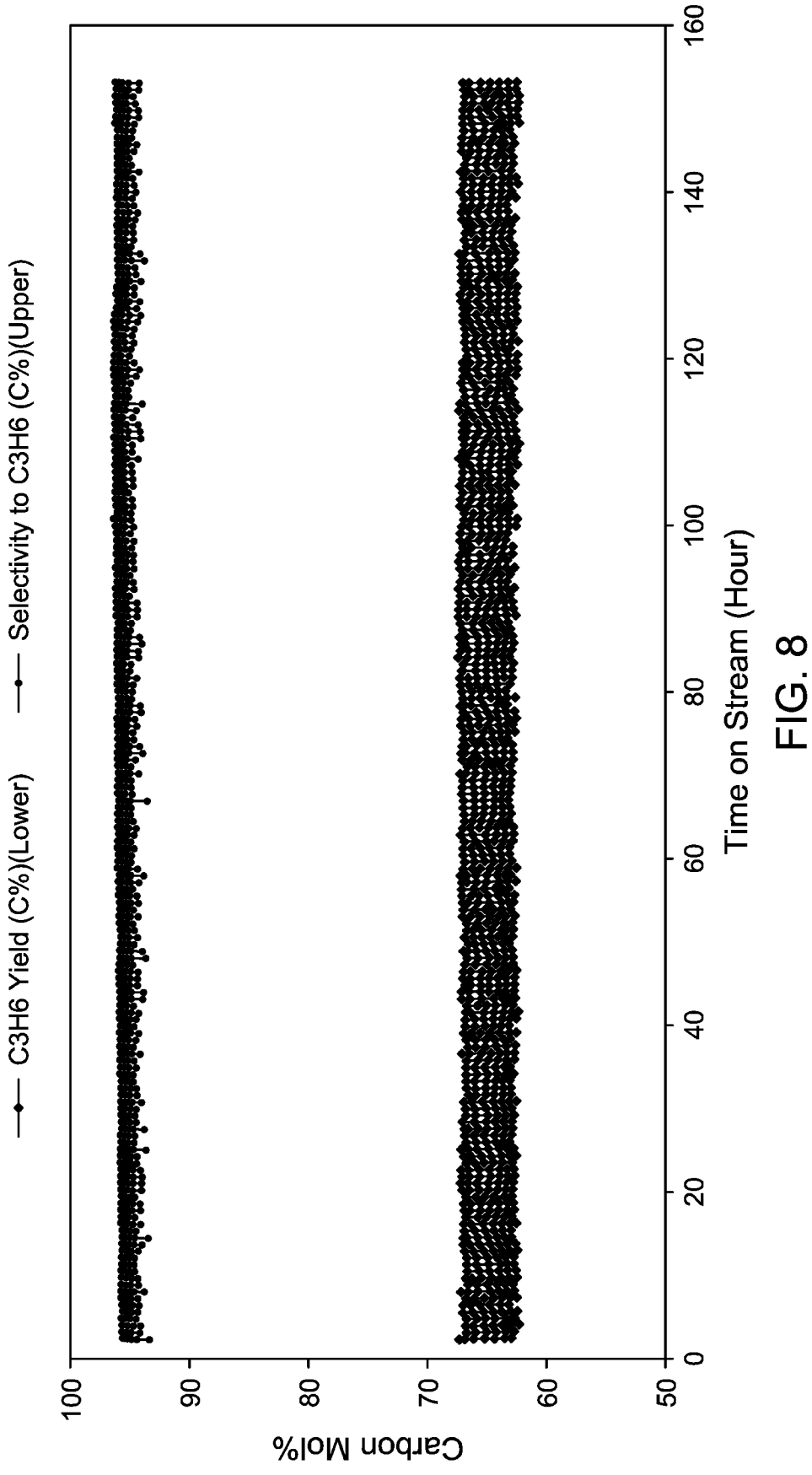
FIG. 8 shows a catalyst composition (catalyst 8) maintained its performance for 204 cycles.

Catalyst 8 that contained only 0.025 wt % of Pt and 1 wt % of Sn was also subjected to a longevity test using the same process steps 1-7 described above with regard to catalysts 3 to 10, except a flow rate of 17.6 sccm was used instead of 35.2 sccm in step 7. FIG. 8 shows that catalyst 8 maintained performance for 204 cycles (x-axis is time, y-axis is $C_3H_6$ yield and selectivity to $C_3H_6$, both in carbon mole %).

All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

While the present disclosure has been described with respect to a number of embodiments and examples, those skilled in the art, having benefit of this disclosure, will appreciate that other embodiments can be devised which do not depart from the scope and spirit of the present disclosure.

What is claimed is:

1. A method for forming an olefin, the method comprising:

introducing a hydrocarbon feed stream into a reactor including a dehydrogenation catalyst;

reacting the hydrocarbon feed stream with the dehydrogenation catalyst in the reactor to form a high temperature dehydrogenated product, the high temperature dehydrogenated product including at least a portion of the dehydrogenation catalyst;

separating at least a portion of the dehydrogenation catalyst from the high temperature dehydrogenated product in a primary separation device and a secondary separation device downstream of and in fluid communication with the primary separation device;

following the exit of high temperature dehydrogenation product from the secondary separation device, combining the high temperature dehydrogenation product with a quench stream, to cool the high temperature dehydrogenation product and form an intermediate temperature dehydrogenation product, wherein the quench stream includes a hydrocarbon and wherein the combining of the high temperature dehydrogenation product with the quench stream occurs within a plenum section of the reactor; and cooling the intermediate temperature dehydrogenation product to form a cooled dehydrogenation product.

2. The method of claim 1, wherein said quench stream includes a liquid hydrocarbon and said intermediate temperature product is completely in a vapor phase.

3. The method of claim 1, wherein the combining includes combining the high temperature dehydrogenation product from a plurality of secondary separation devices with the quench stream, at a location within the plenum that minimizes secondary catalytic cracking within the high temperature dehydrogenation product.

4. The method of claim 1, wherein the quench stream comprises aromatics which are not formed in the high temperature dehydrogenated product.

5. The method of claim 1, further comprising further cooling of the intermediate temperature dehydrogenation product downstream of the reactor, to obtain the cooled dehydrogenation product with a heat exchanger or a secondary quench stream, wherein the quench stream includes at least a portion of the cooled dehydrogenation product after having been further cooled by the heat exchanger or the secondary quench stream.

6. The method of claim 1, wherein the quench stream is not provided to an output region of the primary separation device.

7. The method of claim 1, wherein the primary separation device and the second separation device are each a cyclone separator, and together they remove at least 98% of the dehydrogenation catalyst present in the high temperature dehydrogenated product.

8. The method of claim 1, wherein the hydrocarbon feed is propane, the olefin is propylene, and the dehydrogenation catalyst includes a PtSn/MgO catalyst, with Pt content ranging from 0.001 wt % to 6 wt %, Sn content 0 wt % to 10 wt %, and the catalyst meets requirements of a Geldart A or Geldart B classification, and a reaction temperature within the reactor is 600° C. to 700° C.

9. The method of claim 1, wherein the high temperature dehydrogenation product is at least 620° C.

10. The method of claim 1, wherein the intermediate temperature dehydrogenation product is no greater than 620° C.

11. The method of claim 1, wherein a residence time of the high temperature dehydrogenation product in each of the primary separation device and the secondary separation device is less than one second.

12. The method of claim 1, wherein:

the dehydrogenation catalyst comprises Pt, an inorganic support, and a contaminant, wherein the Pt has a concentration in the range of from 0.001 wt % to 6 wt %, based on the weight of the inorganic support, the inorganic support comprises at least 0.5 wt % of a Group 2 element, based on the weight of the inorganic support, the Group 2 element comprises Mg, at least a portion of the Group 2 element is in a form of MgO or a mixed metal oxide comprising Mg, and the catalyst further comprises up to 10 wt % of a promoter, based on weight of the inorganic support, and wherein the promoter comprises one or more of the following elements: Sn, Ag, Cu, a combination thereof, or a mixture thereof.

13. A system for forming an olefin from a hydrocarbon feed stream, the system comprising:

a reactor configured to receive the hydrocarbon feed stream under reaction conditions with a dehydrogenation catalyst, wherein the reaction conditions generate a high temperature dehydrogenated product, the high temperature dehydrogenated product including at least a portion of the dehydrogenation catalyst;

a plurality of separation devices configured to separate at least a portion of the dehydrogenation catalyst from the high temperature dehydrogenated product, the plurality of separation devices including a primary separation device and a secondary separation device downstream of and in fluid communication with the primary separation device;

a quench system configured to combine the high temperature dehydrogenation product with a quench stream to cool the high temperature dehydrogenation product and form an intermediate temperature dehydrogenation product, wherein the quench stream includes a hydrocarbon, and wherein the quench system is configured to combine the high temperature dehydrogenation product with the quench stream within a plenum section of the reactor; and a heat transfer system configured to cool the intermediate temperature dehydrogenation product to form a cooled dehydrogenation product.

14. The system of claim 13, wherein said quench stream includes a liquid hydrocarbon and said intermediate temperature product is completely in a vapor phase.

15. The system of claim 13, wherein quench system is configured to inject the quench stream at a location within the plenum section that minimizes secondary catalytic cracking within the high temperature dehydrogenation product.

16. The system of claim 13, wherein the heat transfer system includes a heat exchanger or a nozzle configured to supply a secondary quench stream.

17. The system of claim 13, wherein the quench system is configured to not provide the quench stream to an output region of the primary separation device.

18. The system of claim 13, wherein the primary separation device and the second separation device are each a cyclone separator, and together they are configured to remove at least 98% of the dehydrogenation catalyst present in the high temperature dehydrogenated product.

* * * * *